United States Patent [19]

Schwarze et al.

[11] Patent Number: 4,520,209

[45] Date of Patent: May 28, 1985

[54] PROCESS FOR CYCLIZING UPSILON-CHLOROCARBOXYLIC ACIDS

[75] Inventors: Werner Schwarze, Frankfurt; Axel Kleemann, Hanau; Hans Remmel, Freigericht; Wolfgang Hohn, Gründau, all of Fed. Rep. of Germany

[73] Assignee: Degussa Aktiengesellschaft, Frankfurt am Main, Fed. Rep. of Germany

[21] Appl. No.: 625,188

[22] Filed: Jun. 28, 1984

Related U.S. Application Data

[63] Continuation of Ser. No. 195,832, Oct. 10, 1980, abandoned.

[30] Foreign Application Priority Data

Oct. 11, 1979 [DE] Fed. Rep. of Germany ....... 2941211

[51] Int. Cl.$^3$ ............................................... C07C 69/74
[52] U.S. Cl. .................................................. 560/124
[58] Field of Search ........................ 560/124; 562/506

[56] References Cited

U.S. PATENT DOCUMENTS

| | | | |
|---|---|---|---|
| 3,077,496 | 2/1963 | Julia | 560/124 |
| 3,123,629 | 3/1964 | Julia | 560/124 |
| 3,354,196 | 11/1967 | Julia | 560/124 |
| 3,652,652 | 3/1972 | Julia | 560/124 |
| 3,711,549 | 1/1973 | Phillips | 560/124 |

FOREIGN PATENT DOCUMENTS 2008110  5/1979  United Kingdom ................ 560/124

OTHER PUBLICATIONS

Bunce, Organic Preparation and Procedures, Int., 6, pp. 193–196 (1974).
Roberts, "An Introduction to Modern Experimental Organic Chemistry," pp. 14–15, 20 & 21, (1969).
Allinger, "Organic Chemistry," pp. 288–294, (1972).

*Primary Examiner*—Michael L. Shippen
*Attorney, Agent, or Firm*—Cushman, Darby & Cushman

[57] ABSTRACT

γ-chlorocarboxylic acid methyl or ethyl esters are cyclized to the corresponding cyclopropane carboxylic acid esters by employing the sodium or potassium alcoholate of methanol or ethanol in the presence of the same alcohol at a temperature above the boiling point of the alcohol employed.

10 Claims, No Drawings

PROCESS FOR CYCLIZING UPSILON-CHLOROCARBOXYLIC ACIDS

This is a continuation of application Ser. No. 195,832 filed Oct. 10, 1980, now abandoned.

BACKGROUND OF THE INVENTION

The present invention is directed to an improved process for the production of methyl and ethyl esters of cyclopropane carboxylic acids, by, in a given case continuously, cyclizing γ-chlorocarboxylic acid methyl and ethyl esters (i.e. methyl and ethyl esters of γ-chloroalkanoic acids) in the presence of an alcoholate and an alcohol at elevated temperature.

Esters of cyclopropane carboxylic acids are valuable intermediate products for the production of agrochemicals, especially insecticides, and pharmaceutical chemicals.

It is known to condense the ethyl ester of 4-chlorobutyric acid with aqueous potassium hydroxide on pumice. There is obtained thereby in moderate yield the ethyl ester of cyclopropane carboxylic acid besides the free acid and γ-butyrolactone (Rambaud, BL. [5] (1938), pages 1552, 1564).

It is also known to cyclize esters using water free alcoholates. For example the ethyl ester of γ-chlorobutyric acid is boiled under refluxed with sodium t-amylate in t-amyl alcohol for four hours. There is obtained the ethyl ester of cyclopropane carboxylic acid in a yield of 45% of theory. If there is used sodium diemthyl benzylate as the condensing agent the yield is 47% of theory. (Julia et al, Bull. Soc. Chimie (France) 1960, pages 306 et seq.).

Furthermore it is known that the cyclization can take place in inert solvents. For example there is described the cyclization of 5-methyl-3-(1-chloroisopropyl)-hex-4-enoate with sodium-t-amylate in benzene to dl-trans-chrysanthemunic acid methyl ester. The yield is 41.8% respectively 53.6% (Julia U.S. Pat. No. 3,077,496, Julia U.S. Pat. No. 3,123,629).

In Phillips U.S. Pat. No. 3,711,549 for the claimed process for the production of aqueous cyclopropylamine in the first step of the process there is formed the reaction of methyl-4-chloro-butyrate with sodium methylate in an inert gas atmosphere in a non-reactive organic liquid under moisture free conditions. The yield of methyl cyclopropanecarboxylate is 92% of theory.

It is also known to condense γ-chlorocaproic acid ester with sodamide in ether for 4 to 5 days and thereby to 2-methylcyclopropanecarboxylic acid esters in a yield of 85% of theory. A similar experiment with α-methyl-γ-chlorbutyric acid ethyl ester gives 1-methyl-cyclopropanecarboxylic acid ethyl ester in a yield of 47.6% (Cannon J. Amer. Chem. Soc. Vol. 81, pages 1660–1666). This same article similarly shows the preparation of ethyl 1,2,2-trimethylcyclopropane-1-carboxylate in a yield of 71.5%.

In Japanese patent application No. J 749-28509 there is described the condensation of γ-chlorobutyric acid ethyl ester with NaH in paraffin. There is obtained ethyl cyclopropanecarboxylate in a yield of 87.9% of theory.

There has further been described the cyclization of 6-bromo-2,3,3-trimethyl-4-hexenoic acid ethyl ester with potassium-t-butoxide in water free tetrahydrofurane to 1-methyl-2-vinyl-3,3-dimethylcyclopropanecarboxylic acid ethyl ester. The yield is 55% of theory (Japanese patent application No. 51-82242).

Bunce et al in "Organic Preparations and Procedures INc.", 6, pages 193–6 (1974) describe the production of ethyl cyclopropanecarboxylate from γ-chlorobutyric acid ethyl ester and sodium ethylate in ethanol. The yield is 66% of theory. G. M. Lampman et al (I. Chem. Eng. Data 14, page 396 (1969)) describe the production of ethyl cyclopropane carboxylate from 4-bromobutyric acid ethyl ester by cyclization with NaH. The yield is 88% of theory.

All of these known processes show that industrially interesting yields can be attained if there is used as the condensation agent sodium hydride, sodamide or alcohol free alcoholate and the process is operated in the absence of non-inert solvents or dispersing agents. If for example the alcoholate in alcohol is used, there occurs a sharp reduction in yield.

In the case of the cyclization of the ethyl ester of γ-chlorobutyric acid with sodium ethylate in ethanol, besides the cyclopropanecarboxylic acid cyclization another reaction proceeds, namely the formation of the 4-ethoxybutyric acid ethyl ester. Furthermore there must be considered recyclizing in the direction of butyrolactone. This explains the poor yield of 66% of theory. This is also true for the methyl ester.

The use of sodium hydride or sodamide is dangerous and expensive. A carrying out of this cyclization process on an industrial scale is very difficult.

Water free (anhydrous) alcoholates likewise are expensive, their handling is very expensive and requires a large industrial expenditure. Dusts of sodium or potassium methylate or ethylate are injurious to health and have a strongly corrosive action. Water free alcoholates hydrolyze easily, thereby the free bases are formed which disturb the cyclization process, since they saponify the starting compounds (esters). If there is used for example sodium methylate in toluene for the cyclization of γ-chlorobutyric acid methyl ester according to Phillips U.S. Pat. No. 3,711,549 on an industrial scale, there is obtained in this process the most finely divided sodium chloride which adheres to the walls of the reactor and as a result considerably disturbs the heat transfer. The result is that in the industrial synthesis there must frequently be used a large excess alkali alcoholate. If condensation is carried out according to this process there is obtained sodium or potassium chloride or bromide in the most finely divided state which immediately encases the sodium or potassium alcoholate so that only a portion of the condensation agent employed is effective. This condition can be partially eliminated if the reaction medium is kept in strong motion and the reaction time increased sharply. In any case additional technical requirement must be used in the process disclosed in the above patent to permit industrial realization thereof.

SUMMARY OF THE INVENTION

It has now been found that γ-chlorocarboxylic acid esters of the general formula I

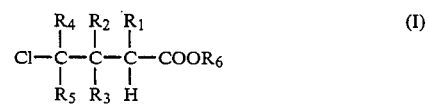

in which $R_1$ through $R_5$ are the same or different and signify either a hydrogen atom or a methyl group and $R_6$ is a methyl or ethyl group can be cyclized to cyclopropanecarboxylic acid esters of the second formula (II)

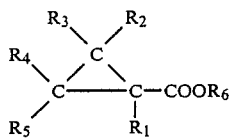

in which $R_1$ through $R_6$ are as defined above, in the presence of an alcoholate as condensation agent and in the presence of a solvent at elevated temperature, if there is used as condensation agent potassium, or preferably sodium methylate and as solvent methyl alcohol, or as condensation agent potassium or preferably sodium ethylate and as solvent ethyl alcohol, and the cyclization is undertaken at a temperature above the boiling point of the alcohol used, in a given case using superatmospheric pressure.

As starting γ-chlorocarboxylic acid esters there can be used for example
methyl 4-chlorobutyrate,
ethyl 4-chlorobutyrate,
methyl-2-methyl-4-chlorobutyrate,
ethyl-2-methyl-4-chlorobutyrate,
methyl-2,4-dimethyl-4-chlorobutyrate,
ethyl-2,4-dimethyl-4-chlorobutyrate,
methyl-2,3,4-trimethyl-4-chlorobutyrate,
ethyl-2,3,4-trimethyl-4-chlorobutyrate,
methyl-4-methyl-4-chlorobutyrate,
ethyl-4-methyl-4-chlorobutyrate,
methyl-3,3-dimethyl-4-chlorobutyrate,
ethyl-3,3-dimethyl-4-chlorobutyrate,
methyl-2,3,3,4,4-pentamethyl-4-chlorobutyrate,
ethyl-2,3,3,4,4-pentamethyl-4-chlorobutyrate,
methyl-2,3,3,4-tetramethyl-4-chlorobutyrate.

Examples of cyclopropanecarboxylic acid esters which can be made according to the invention includes
methyl cyclopropanecarboxylate,
ethyl cyclopropanecarboxylate,
methyl 1-methylcyclopropanecarboxylate,
ethyl 1-methylcyclopropanecarboxylate,
methyl 1,2-dimethylcyclopropanecarboxylate,
ethyl 1,2-dimethylcyclopropanecarboxylate,
methyl 1,2,3-trimethylcyclopropanecarboxylate
ethyl 1,2,3-trimethylcyclopropanecarboxylate,
methyl 2-methylcyclopropanecarboxylate,
ethyl 2-methylcyclopropanecarboxylate,
methyl 1,2,2,3,3-pentamethylcyclopropanecarboxylate,
ethyl 1,2,2,3,3-pentamethylcyclopropanecarboxylate,
methyl 1,2,2,4-tetramethylcyclopropanecarboxylate,
ethyl 1,2,2,4-tetramethylcyclopropanecarboxylate.

According to this process the cyclopropylcarboxylic acid ester can be obtained in very high yields both discontinuously and continuously. They can be converted into the corresponding free acids according to known methods, even without intermediate isolation. Alkali alcoholates in alcohol are industrial chemicals which are easily handled. They can be produced easily and are easily transportable.

Of the alcoholates used sodium methylate and sodium ethylate are preferred. They are employed in equimolar amounts with the γ-chlorocarboxylic acid ester. It is advantageous to use 10% (or even more) excess of the alcoholate.

The process of the invention can be carried out in the temperature range between about 90° C. and about 200° C.

In carrying the process discontinuously one can proceed in such manner that the alkali alcoholate, preferably the sodium methylate or sodium ethylate, is present in a pressure vessel (autoclave). For 1 mole of α-chlorocarboxylic acid ester there is needed 1 mole of alcoholate for the cyclization, but a 10% excess of the cyclizing agent (alcoholate) is suitable. The autoclave is heated to a high temperature. Preferred reaction temperatures are those between about 140 and about 200° C., particularly, however, between about 155 and 160° C. At this temperature the haloester is pumped into the autoclave, thereby the reaction progresses in a few minutes. At the end there is a brief post heating and working up. The amount of alcohol solvent employed is not critical and can be for example 120 to 140 grams per mole of alcoholate.

However, this process can also be carried out at normal pressure (i.e. atmospheric pressure) if the reaction is allowed to progress above the boiling point of the alcohol used. This can be attained for example by using highly concentrated alcoholate solutions (for example 30%) and maintaining the high concentration, (e.g. concentration of 30 to 40%, during the entire progress of the reaction, so that the alcohol formed during the cyclization process is continuously distilled off.

The continuous process preferably takes place in a thin layer evaporator. In this case suitably the solution of alkali alcoholate in alcohol and the γ-chlorobutyric acid ester are pumped separately, or, premixed, in common into the thin layer evaporator. The wall temperature of the jacket, for example heated with oil, should be so regulated that the entering alcohol is immediately evaporated. During this time the cyclization also occurs instantaneously and the ester formed distills off continuously with the alcohol. At the lower discharge end of the thin layer evaporator, the alkali metal chloride, especially sodium chloride, formed in the reaction is continuously drawn off. Preferred wall temperatures are, depending on the material of the evaporator, about 120 to 200° C., especially 170 to 180° C. The mixture of ester and alcohol leaving the reaction thin layer evaporator in this process can for example be worked up continuously over several successively connected distillation columns.

The γ-chlorocarboxylic acid esters needed as starting material for the process of the invention can be produced according to known processes from the corresponding lactones or γ-hydroxycarboxylic acids (Liebigs Ann., 596 pages 163–164 and also Phillips U.S. Pat. No. 3,711,549).

Unless otherwise indicated all parts and percentages are by weight.

The process can comprise, consist essentially of or consist of the stated steps with the materials recited.

DETAILED DESCRIPTION

EXAMPLE 1

There was present in a 5 liter stirred autoclave 540 grams of sodium methylate in 1,500 ml of methanol and this mixture was subsequently heated to 155° to 160° C. Then within 30 minutes there were pumped in 1,228.5 grams of methyl γ-chlorobutyrate and this temperature maintained subsequently for another hour. The autoclave was emptied, treated with methylene chloride, sufficient water added that the sodium chloride formed just dissolved, the CH$_2$Cl$_2$ separated off and the aqueous-methanol solution shaken three times with CH$_2$Cl$_2$. The CH$_2$Cl$_2$ fractions were combined, dried and fractionated on a 1 meter packed column with a deplilequiator.

Methyl cyclopropanecarboxylate distilled at B.P.$_{760}$ 114° to 115° C. Amount: 853.5 grams, corresponding to 94.9% of theory.

EXAMPLE 2

There were present in a 2 liter round bottom flask (equipped with stirrer, attached 50 cm packed column and dephlegmator) 594 grams of a 30% sodium methylate solution in methanol (=3.3 moles of CH$_3$ONa). The solution was heated to boiling. Methanol was distilled off until the methylate solution showed a temperature of 100° C. (135 g).

Then within 2 hours there were slowly dropped in, in all 409.5 grams of methyl γ-chlorobutyrate (=3 moles), thereby there was continuously distilled off methanol (with small amounts of methyl cyclopropanecarboxylate). The running in and the distillation were so programmed that the temperature of the methylate solution never went below 90° C. Subsequently heating was continued for 15 minutes.

The solution in the flask was cooled, neutralized with about 20 grams of glacial acetic acid, 500 ml of methylene chloride added and the mixture diluted with 1 liter of water.

The methylene chloride was mixed with the methanol distilled off in the reaction (+methyl cyclopropanecarboxylate) and fractionated on a 1 meter packed column (with dephlegmator). After a forerun of methylene chloride the methanol distilled first and subsequently methyl cyclopropanecarboxylate, B.P. 114°–115° C. Amount: 277.5 grams, corresponding to a yield of 92.5% of theory.

COMPARISON EXAMPLE

There were present in a 2 liter round bottom flask equipped with stirrer 178.2 grams of sodium methylate in 570 ml of methanol. Within one hour there were dropped under reflux 409.5 grams of methyl γ-chlorobutyrate and the mixture subsequently heated for a further 2 hours under reflux. Then it was worked up as described in Example 1. There were isolated 198.6 grams of methyl cyclopropanecarboxylate, B.P.$_{760}$ 114° to 115° C. Yield 66.2% of theory.

The distillative working up of the residue produced 81 grams of methyl methoxybutyrate (=20.4% of theory) and 36 grams (=8.8% of unreacted methyl γ-chlorobutyrate, as well as 6.1 grams of γ-butyrolactone).

EXAMPLE 3

1.365 kg of methyl γ-chlorobutyrate (=10 moles) and 494 grams of sodium methylate dissolved in 1386 grams of methanol (=30% solution) were continuously fed from two separate supply vessels via 2 pumps into a reaction evaporator (thin layer evaporator) heated by means of an oil heated jacket, whereby the speed was so regulated that there were reacted per 15 minutes 1 mole of methyl γ-chlorobutyrate. The rotor of the reactor ran with a number of revolutions which provided that the continuously supplied reactants evaporated in a few seconds and the cyclization then occurred chiefly in the upper half of the evaporator. There was continuously drawn off at the lower end of the apparatus solid salt, mixed with excess alcoholate, at the top there were continuously drawn off methanol and methyl cyclopropanecarboxylate.

The reaction was finished in 2½ hours, subsequently there were evaporated in the reactor a further 500 ml of CH$_3$OH.

the continuously distilling off mixture of CH$_3$OH and methyl cyclopropanecarboxylate was worked up discontinuously, however, it is also possible to work up continuously.

At B.P.$_{760}$ 114° C. methyl cyclopropanecarboxylate distilled. Amount: 915 grams=91.5% of theory.

EXAMPLE 4

The procedure was as described in Example 3 but there was reacted 1.505 kg of methyl γ-chlorovalerate with 1.98 kg of 30% sodium methylate solution in CH$_3$OH. The working up yielded 1,029 grams of methyl 2-methylcyclopropanecarboxylate, B.P. 131° C.

EXAMPLE 5

The procedure was as described in Example 3 but there were reacted 1.505 kg of methyl 1-methyl-γ-chlorobutyrate and 1.98 kg of 30% sodium methylate in methanol.

There was obtained: 991 grams=87% of theory of methyl 1-methyl cyclopropanecarboxylate, B.P. 136° C.

EXAMPLE 6

The procedure was as described in Example 1 but there were reacted 1.505 kg of ethyl γ-chlorobutyrate and 4 kg of a 18.7% sodium ethylate solution in ethanol.

There were obtained: 1,040 grams=91.2% of theory of ethyl cyclopropanecarboxylate, B.P. 131° to 132° C.

EXAMPLE 7

409.5 kg of methyl γ-chlorobutyrate (=3000 moles) were cyclized with 3,300 moles of CH$_3$ONa (=594 kg) in methanol in a 2m$^3$ reactor under the experimental conditions set forth in Example 2.

After the cyclization the methanol formed in the reaction together with the methyl cyclopropanecarboxylate which distilled over were returned to the reactor. The gas chromatographic analysis of the solution showed that the cyclization proceeded quantitatively. Then there were slowly flowed in 300 kg of 50% aqueous sodium hydroxide. The mixture was boiled for 2 hours under reflux. Methanol was subsequently distilled over a column. The reactor residue was cooled off to 10° C., treated with 400 liters of methylene chloride and subsequently adjusted with concentrated hydrochloric acid (Ca 36%) to pH 2 (about 70 liters).

The methylene chloride solution was separated off. Subsequently the aqueous solution was extracted twice, each time with 200 liters of CH$_2$Cl$_2$.

The CH$_2$Cl$_2$ solutions were distilled. The cyclopropanecarboxylic acid remaining was fractioniated on a 2 m-column.

B.P.$_{10}$ 78° C., amount: 235 kg corresponding to 96.7% of theory.

What is claimed is:

1. A process for the cyclization of a α-chlorocarboxylic acid ester of the formula

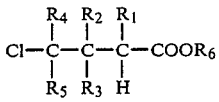

where each of $R_1$ to $R_5$ is hydrogen or the methyl group and $R_6$ is methyl or ethyl to cyclopropanecarboxylic acid ester of the formula

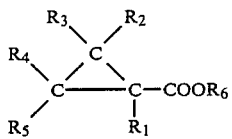

comprising carrying out the reaction employing as condensation agent sodium or potassium methylate and as solvent methyl alcohol or employing as condensation agent sodium or potassium ethylate and as solvent ethyl alcohol at a temperature above the boiling temperature of the alcohol used and between 90° and 200° C., said process including the steps of continuously feeding the reactants to a thin layer evaporator and continuously evaporating them in the evaporator and continuously drawing off from the top of the evaporator the cyclopropanecarboxylic acid ester formed continuously drawing off at the lower end of the evaporator the salt formed.

2. The process of claim 1 where all of $R_1$ through $R_5$ are hydrogen or one of $R_1$ through $R_5$ is methyl.

3. The process of claim 2 where all of $R_1$ through $R_5$ are hydrogen.

4. The process of claim 2 wherein either $R_1$ or $R_4$ is methyl and the remaining member of $R_1$ to $R_5$ are hydrogen.

5. The process of claim 1 wherein there is employed sodium methylate or sodium ethylate.

6. The process of claim 1 wherein the alcoholate is employed in a molar amount at least equal to that of the chlorocarboxylic acid ester.

7. The process of claim 6 wherein the alcoholate is used in a molar excess of at least 10%.

8. The process of claim 6 wherein the solvent is methyl alcohol.

9. The process of claim 1 wherein the temperature is between 140° and 200° C.

10. The process of claim 13 wherein the temperature is between 155° and 160° C.

* * * * *

UNITED STATES PATENT AND TRADEMARK OFFICE
CERTIFICATE OF CORRECTION

PATENT NO. : 4,520,209
DATED : May 28, 1985
INVENTOR(S) : SCHWARZE ET AL

It is certified that error appears in the above-identified patent and that said Letters Patent is hereby corrected as shown below:

IN THE TITLE:

Change "UPSILON" to --GAMMA--.

IN THE CLAIMS:

Claim 1, column 6, line 67, change "$\alpha$" to --$\gamma$--.

Claim 10, line 1, change "13" to --9--.

Signed and Sealed this

Tenth Day of December 1985

[SEAL]

Attest:

DONALD J. QUIGG

Attesting Officer     Commissioner of Patents and Trademarks